(12) United States Patent
Wiseall et al.

(10) Patent No.: US 9,945,716 B2
(45) Date of Patent: Apr. 17, 2018

(54) DETERMINATION OF ULTRASONIC INSPECTABILITY

(71) Applicant: ROLLS-ROYCE PLC, London (GB)

(72) Inventors: Stephen Samuel Wiseall, Derby (GB); Anthony Bernard Phipps, Derby (GB); David Cameron Wright, Loughborough (GB); Sree Vamsi Tammineni, Wilmslow (GB); James William Cheang Meas, Bristol (GB)

(73) Assignee: ROLLS-ROYCE plc, London (GB)

( * ) Notice: Subject to any disclaimer, the term of this patent is extended or adjusted under 35 U.S.C. 154(b) by 287 days.

(21) Appl. No.: 14/856,160

(22) Filed: Sep. 16, 2015

(65) Prior Publication Data

US 2016/0103013 A1  Apr. 14, 2016

(30) Foreign Application Priority Data

Oct. 8, 2014 (GB) .................................. 1417762.0

(51) Int. Cl.
*G01H 1/00* (2006.01)
*G01N 29/04* (2006.01)
*G01N 29/44* (2006.01)

(52) U.S. Cl.
CPC ........... *G01H 1/006* (2013.01); *G01N 29/043* (2013.01); *G01N 29/4472* (2013.01)

(58) Field of Classification Search
None
See application file for complete search history.

(56) References Cited

U.S. PATENT DOCUMENTS

| 7,017,414 | B2* | 3/2006 | Falsetti | G01N 29/11 73/600 |
| 2008/0047122 | A1* | 2/2008 | Falsetti | G01N 29/043 29/407.01 |
| 2014/0259598 | A1* | 9/2014 | Lipschutz | G01M 5/0016 29/407.01 |
| 2015/0278727 | A1* | 10/2015 | Sankaran | G06Q 10/0633 705/7.27 |

FOREIGN PATENT DOCUMENTS

EP  1710570 A1  10/2006

OTHER PUBLICATIONS

Mar. 19, 2015 Search Report issued in Great Britian Application No. 1417762.0.

* cited by examiner

*Primary Examiner* — Paul West
*Assistant Examiner* — Mark A Shabman
(74) *Attorney, Agent, or Firm* — Oliff PLC

(57) ABSTRACT

The ultrasonic inspectability of a supplied part out of which a final component is to be machined is determined by following a set of inspection rules for ultrasonic inspection of the supplied part. The rules determine which parts of the polygon cannot be inspected by a scan at a given ultrasound beam angle (typical beam angles are 0°, +20° and −20° relative to the perpendicular direction to the edge) along a given edge of the polygon.

13 Claims, 14 Drawing Sheets

DETERMINATION OF ULTRASONIC INSPECTABILITY

FIELD OF THE INVENTION

The present invention relates to a method of determining the ultrasonic inspectability of a supplied part out of which a final component is to be machined.

BACKGROUND OF THE INVENTION

A typical manufacturing process for a component of, e.g. a gas turbine engine, involves producing a forging, heat-treating the forging, and then machining the forging to produce the final component. The forging is thus a supplied part that envelopes the material of the final component.

Components formed in this way can be high value and safety critical, such as rotor discs. They are commonly ultrasonically inspected to detect anomalies that may be introduced by melting, forging and heat treatment processes before final machining. If an anomaly is detected, the component may be scrapped.

If a component is to be scrapped, it is preferable from a cost point of view that the anomaly is detected as early in the manufacturing process as possible. Accordingly, ultrasonic inspection is often performed on the supplied part, e.g. the heat-treated forging envelope, rather than on the final machined component. Also, the surface geometry of the supplied part is generally simpler than that of the final component, making ultrasonic inspection of the supplied part correspondingly simpler.

SUMMARY OF THE INVENTION

To ensure consistency and quality, ultrasonic inspection is generally performed by trained inspectors. In addition, rules may be applied before inspection to the supplied part to ensure the inherent inspectability of the material of the final component within the part. To apply the rules, the supplied part may be represented as one or more 2D polygons. In the case of an axisymmetric component and supplied part (e.g. a rotor disc, such as a gas turbine engine rotor disc), this polygon can be simply a single longitudinal cross-section. In the case of more complex, non-axisymmetric parts (e.g. a combustion case outer casing or a high-pressure turbine casing of a gas turbine engine), a number of cross-sections may be needed to represent the part. The rules determine which parts of the polygon cannot be inspected by a scan at a given ultrasound beam angle (typical beam angles are 0°, +20° and −20° relative to the perpendicular direction to the edge) along a given edge of the polygon. An example of the rules for a scan are as follows:

Near surface resolution limits at the given edge prevent inspection of the material immediately beneath the edge to a given depth.

Non-inspectable regions caused by diffraction and reduced signal return are defined at internal convex vertices of the polygon.

Non-inspectable standoff regions caused by signal noise are defined in front of other edges which are parallel to the ultrasound beam direction, the extent of the standoff increasing with beam penetration depth.

Far surface resolution limits prevent inspection of the material immediately beneath other edges of the polygon to a given depth.

By "beam angle" we mean the ultrasound beam angle within the scanned supplied part. For beam angles which are not 0°, this is not generally the same as the angle at which the ultrasound is emitted from the ultrasonic probe because of refraction of the ultrasound beam at the surface of the part. For example, to produce a beam angle of 20° within a supplied part formed of Waspalloy, the bean should generally be emitted from the probe at an angle of 5°.

A further rule may require that any given point within the material of the supplied part which forms the final component must be inspectable by at least a minimum number of different scans. For example, if a point is inspectable by at least three different scans, then there is a high probability that an anomaly at that point will be detected by ultrasonic inspection even if it is, e.g., orientated in such a way as to be missed by one or even two of the scans.

However, in order to facilitate a process of designing an appropriate supplied part for a final component, it would be desirable to be able to determine quickly and easily the ultrasonic inspectability of a supplied part.

Accordingly, in a first aspect, the present invention provides a method of determining the ultrasonic inspectability of a supplied part out of which a final component is to be machined, the method including the steps of:

providing a set of inspection rules for ultrasonic inspection of the supplied part;

providing an input geometry for the supplied part in the form of at least one 2D polygon, the supplied part being ultrasonically inspectable by scanning an ultrasonic probe at one or more different ultrasound beam angles along faces of the supplied part corresponding to polygon edges of the input geometry, whereby a complete ultrasonic inspection of the supplied part comprises a number of scans equal to the sum, over all the edges, of all the beam angles used for a given edge;

providing a target geometry which is at least one further 2D form defining the shape and position of the machined final component within the input geometry;

for each edge of the input geometry, determining a respective allowable region of the input geometry that defines those parts of the input geometry which can be ultrasonically inspected from that edge without infringing the inspection rules;

for each combination of a given ultrasound beam angle and a given edge of the input geometry, determining a respective limitation shape which is bounded at one side by the given edge and extends from that edge in the direction of the beam to a boundary at a penetration depth of the ultrasound in the input geometry;

for each edge of the input geometry, combining the one or more limitation shapes for that edge with the allowable region for that edge to determine one or more inspectable regions of the input geometry associated with that edge, each inspectable region thereby corresponding to a respective one of the scans of the complete ultrasonic inspection; and overlaying the inspectable regions in their relative positions on the target geometry, whereby the supplied part is determined to be ultrasonically inspectable when all parts of the target geometry are overlayed by at least a predetermined minimum number of the inspectable regions.

Advantageously, the method can systematically and efficiently combine inspection rules and ultrasound penetration limits at each edge of the input geometry to determine inspectable regions at each edge, and then by overlaying these regions enable a determination of whether the supplied part is ultrasonically inspectable. The method can be computer-implemented.

Further aspects of the present invention provide: a computer program comprising code which, when run on a computer, causes the computer to perform the method of the first aspect; a computer readable medium storing a computer program comprising code which, when run on a computer, causes the computer to perform the method of the first aspect; and a computer system programmed to perform the method of the first aspect. For example, a computer system can be provided for determining the ultrasonic inspectability of a supplied part out of which a final component is to be machined, the system including:

a computer-readable medium or media which stores: (i) a set of inspection rules for ultrasonic inspection of the supplied part; (ii) an input geometry for the supplied part in the form of at least one 2D polygon, the supplied part being ultrasonically inspectable by scanning an ultrasonic probe at one or more different ultrasound beam angles along faces of the supplied part corresponding to polygon edges of the input geometry, whereby a complete ultrasonic inspection of the supplied part comprises a number of scans equal to the sum, over all the edges, of all the beam angles used for a given edge; and (iii) a target geometry which is at least one further 2D form defining the shape and position of the machined final component within the input geometry; and one or more processors operatively connected to the computer-readable medium or media, and configured to perform the steps of: (i) for each edge of the input geometry, determine a respective allowable region of the input geometry that defines those parts of the input geometry which can be ultrasonically inspected from that edge without infringing the inspection rules; (ii) for each combination of a given ultrasound beam angle and a given edge of the input geometry, determine a respective limitation shape which is bounded at one side by the given edge and extends from that edge in the direction of the beam to a boundary at a penetration depth of the ultrasound in the input geometry; (iii) for each edge of the input geometry, combine the one or more limitation shapes for that edge with the allowable region for that edge to determine one or more inspectable regions of the input geometry associated with that edge, each inspectable region thereby corresponding to a respective one of the scans of the complete ultrasonic inspection; and (iv) overlay the inspectable regions in their relative positions on the target geometry, whereby the supplied part is determined to be ultrasonically inspectable when all parts of the target geometry are overlayed by at least a predetermined minimum number of the inspectable regions. The system thus corresponds to the method of the first aspect. The system may further include: a display device for displaying any one or more of: the input geometry, the target geometry, and the overlayed inspectable regions.

A further aspect of the present invention provides a manufacturing process including the steps of: designing a supplied part; performing the method of the first aspect to determine that the supplied part is ultrasonically inspectable; producing the supplied part; and ultrasonically inspecting the supplied part. The process may further include the step of machining the inspected supplied part to produce the final component therefrom.

Optional features of the invention will now be set out. These are applicable singly or in any combination with any aspect of the invention.

The supplied part and the final component may be axisymmetric. The input geometry can then be a longitudinal cross-section through the supplied part, and the target geometry can be a longitudinal cross-section through the final component. For example, the final component may be a rotor disc of a gas turbine engine.

Alternatively, the supplied part and/or the final component may be non-axisymmetric. The input geometry can then be plural longitudinal cross-sections through the supplied part, and the target geometry can be plural longitudinal cross-sections through the final component. For example, the final component may be combustion case outer casing or a high-pressure turbine casing of a gas turbine engine. The supplied part may typically be a forging that envelopes the material of the final component. However, other types of supplied parts are also possible, for example parts produced from powder by hot isostatic pressing.

The input geometry for the supplied part may be provided in the form of at least one rectilinear 2D polygon. A rectilinear input geometry can facilitate ultrasonic inspection of the, typically more complex, target geometry.

The combining step can include the sub-step of calculating, for each combination of a limitation shape and the allowable region, the intersection polygon of that limitation shape with the allowable region. Each inspectable region may be that basic intersection polygon. However, the combining step can further include the sub-step of cropping the intersection polygon to remove parts thereof which cannot be penetrated by the ultrasound beam due to obstructions. The combining step can further include the sub-step of trimming the intersection polygon to remove parts thereof which cannot be penetrated by the ultrasound beam due to the finite beam width.

BRIEF DESCRIPTION OF THE DRAWINGS

Embodiments of the invention will now be described by way of example with reference to the accompanying drawings in which.

DETAILED DESCRIPTION AND FURTHER OPTIONAL FEATURES OF THE INVENTION

Overview

Figure 1:
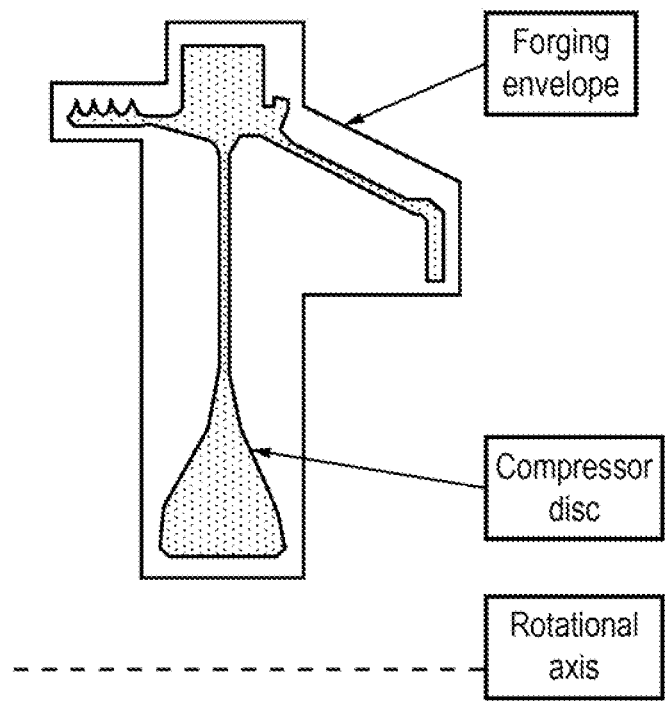
FIG. 1 shows schematically longitudinal cross-sections through a compressor disc of a gas turbine engine and a supplied part forging envelope for the disc.

FIG. 1 shows schematically longitudinal cross-sections through a compressor disc of a gas turbine engine and a supplied part forging envelope for the disc. The envelope cross-section is in the form of a rectilinear 2D polygon (hereafter termed the "input geometry"). The disc, which is machined from the forging envelope, has a cross-section which is also a 2D form (hereafter termed the "target geometry").

Figure 2:
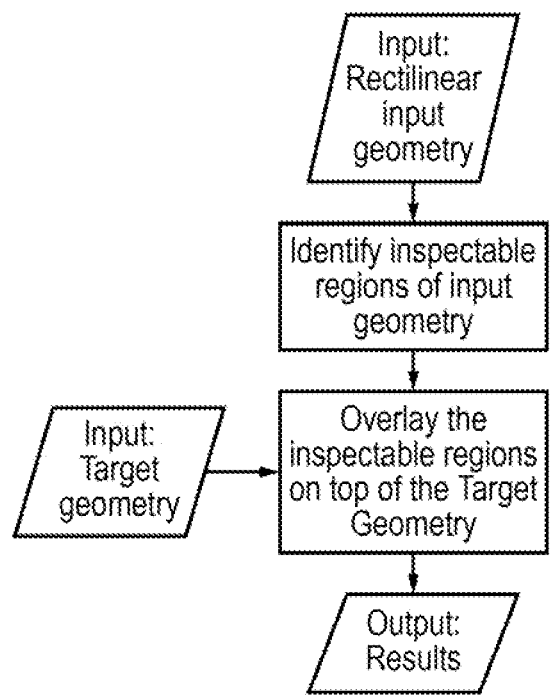
FIG. 2 is a flow chart showing an overview of a process for determining the ultrasonic inspectability of a target geometry.

The rectilinear input geometry facilitates ultrasonic inspection of the, typically more complex, target geometry with an appropriate number of scans from a number of different directions. FIG. 2 is a flow chart showing an overview of a process for determining the ultrasonic inspectability of the target geometry.

Figure 3:
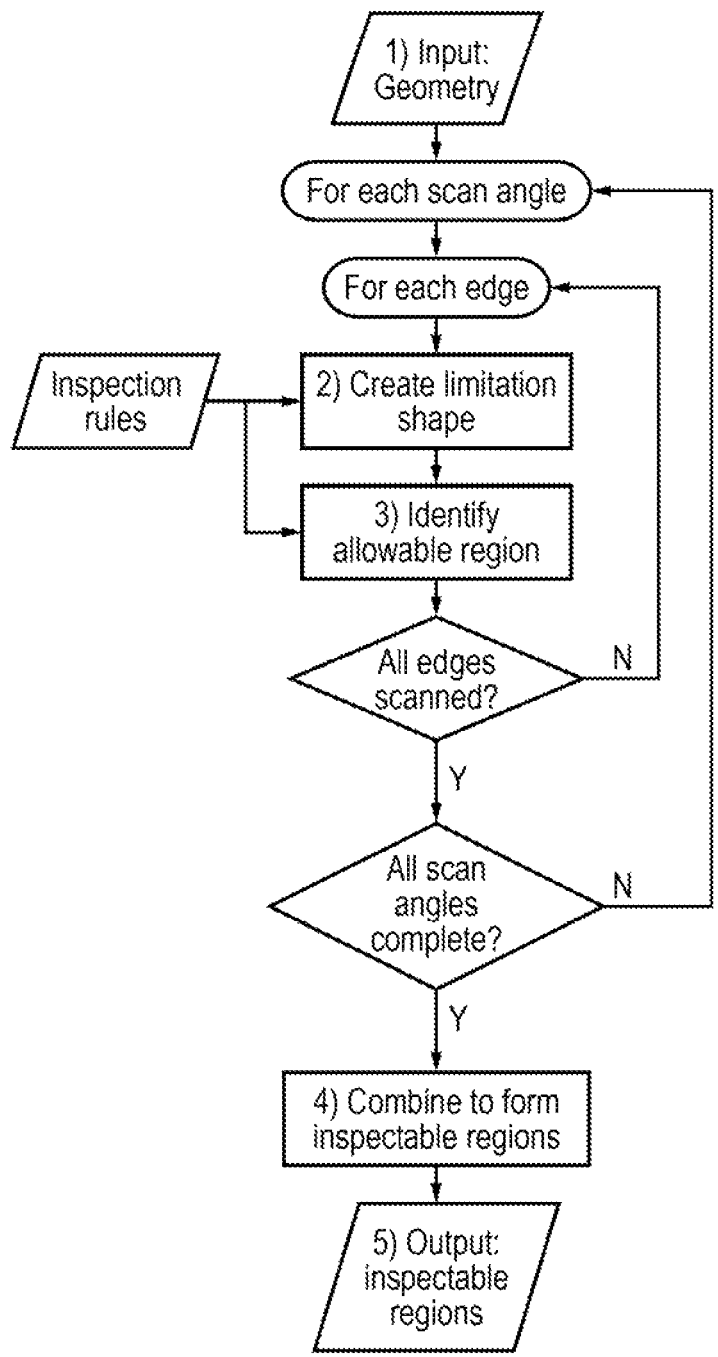
FIG. 3 is a flow chart showing more detail of the "Identify" step of FIG. 2.

To identify whether the design of the input geometry allows inspection of the target geometry, it is analysed using a set of inspection rules. These rules provide a high level of confidence that anomalies of a particular size can be detected within the inspection region. The input geometry is also analysed for penetrability by ultrasound. These analyses are performed in the "Identify" step of FIG. 2. FIG. 3 is a flow chart showing more detail of that step.

Stage 1) of the flow chart of FIG. 3 is to receive the input geometry. Then for each edge of the input geometry and for each beam angle of the ultrasound beam limitation shapes and allowable regions are determined (stages 2) and 3)). For example, if each edge of an N-sided input geometry is scanned at three beam angles (e.g. 0°, +20° and −20° relative to the perpendicular direction to the edge), then there will be 3N limitation shapes (i.e. one for each beam angle/edge combination) and N allowable regions (i.e. one for each edge). The allowable regions of the input geometry defines those parts of the input geometry which can be ultrasonically inspected from their respective edges without infringing the inspection rules. Each limitation shape is bounded at one side by its respective edge and extends from that edge in the direction of the beam to a boundary at a penetration depth of the ultrasound in the input geometry. The penetration depth and other optional refinements of the limitation shapes may also be specified by the inspection rules. The determinations of the limitation shapes and allowable regions are discussed in more detail below. Having determined limitation shapes and allowable regions, they are combined in stage 4) and then made available in stage 5) for the determination of which parts of the target geometry are ultrasonically inspectable. These stages are also discussed in more detail below.

Determination of the Allowable Regions

An example of the inspection rules applied to the edges of an input geometry are:

Near surface resolution limits at a given edge prevent inspection of the material immediately beneath the edge to a given depth.

Non-inspectable caused by diffraction and reduced signal return are defined at internal convex vertices of the input geometry.

Non-inspectable standoff regions caused by signal noise are defined in front of other edges which are parallel to the ultrasound beam direction, the extent of the standoff increasing with beam penetration depth.

Far surface resolution limits prevent inspection of the material immediately beneath other edges of the input geometry to a given depth.

Figure 4:
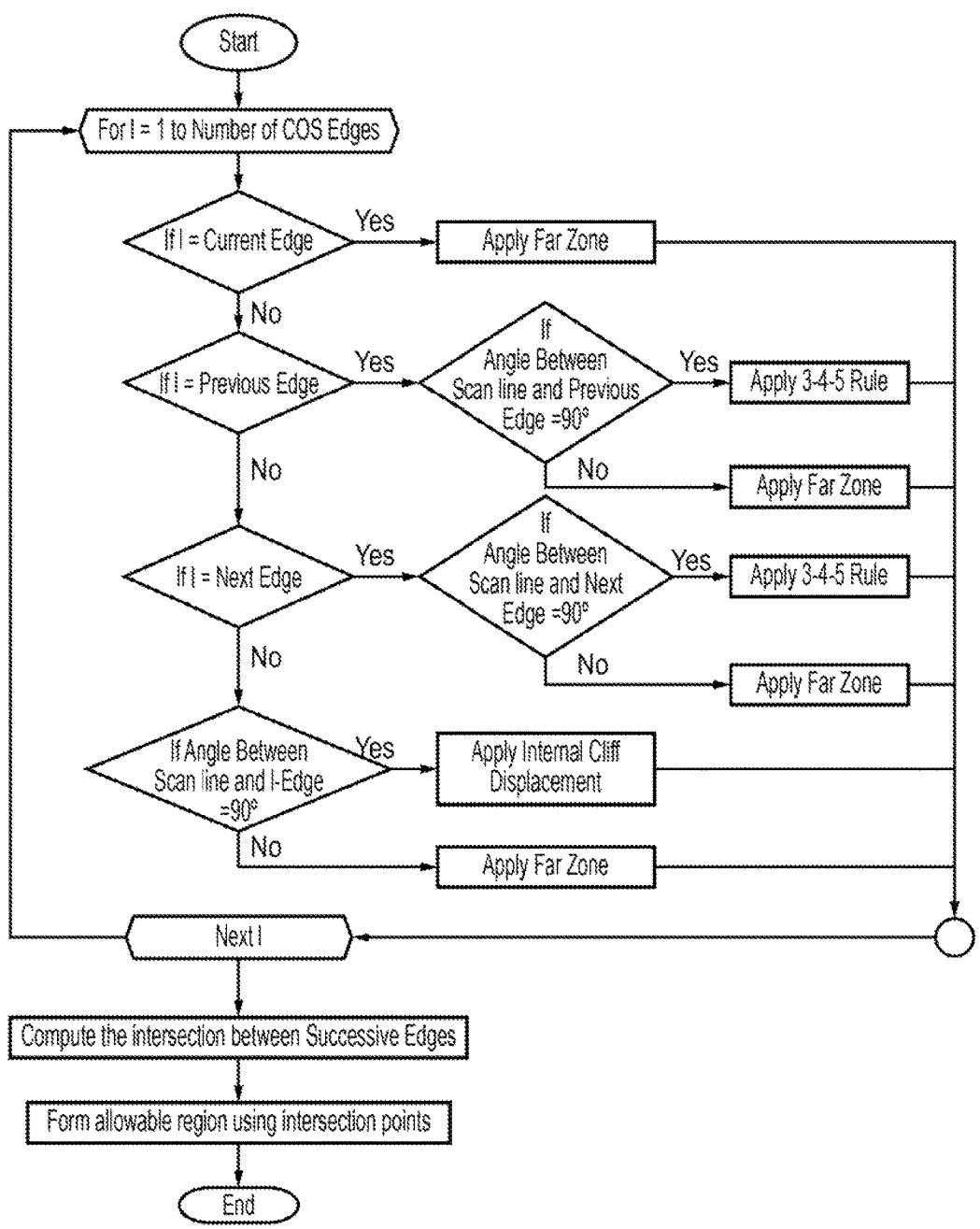
FIG. 4 is a flow chart describing a procedure for determining, for a given edge of an input geometry, an allowable region from inspection rules.

FIG. 4 is a flow chart describing a procedure for determining an allowable region for a given edge (the "current edge") from such rules. In the flow chart:

"COS" stands for "condition of supply", and is the input geometry.

The 3-4-5 rule defines a non-scannable region at internal convex vertices at the ends of neighbouring edges which are parallel to the ultrasound beam direction. In particular, specific beam radial resolutions, e.g. 3, 4 or 5 mm, are applied either side of vertices.

"Internal cliff displacement" produces the non-inspectable standoff regions which are defined in front of other edges parallel to the ultrasound beam direction.

"Apply Far Zone" is a procedure which applies the near or far surface resolution limit, as the case may be.

The procedure loops around each edge of the input geometry, applying the appropriate rule to each edge. As a result each edge is modified to some extent. The final stages of the procedure then compute the intersections between the successive modified edges, and form the allowable region for the given edge from these intersections. The procedure is repeated N times for an input geometry having N edges to produce the N allowable regions, at each repeat a next edge being the "current edge".

Determination of the Limitation Shapes

Figure 5:
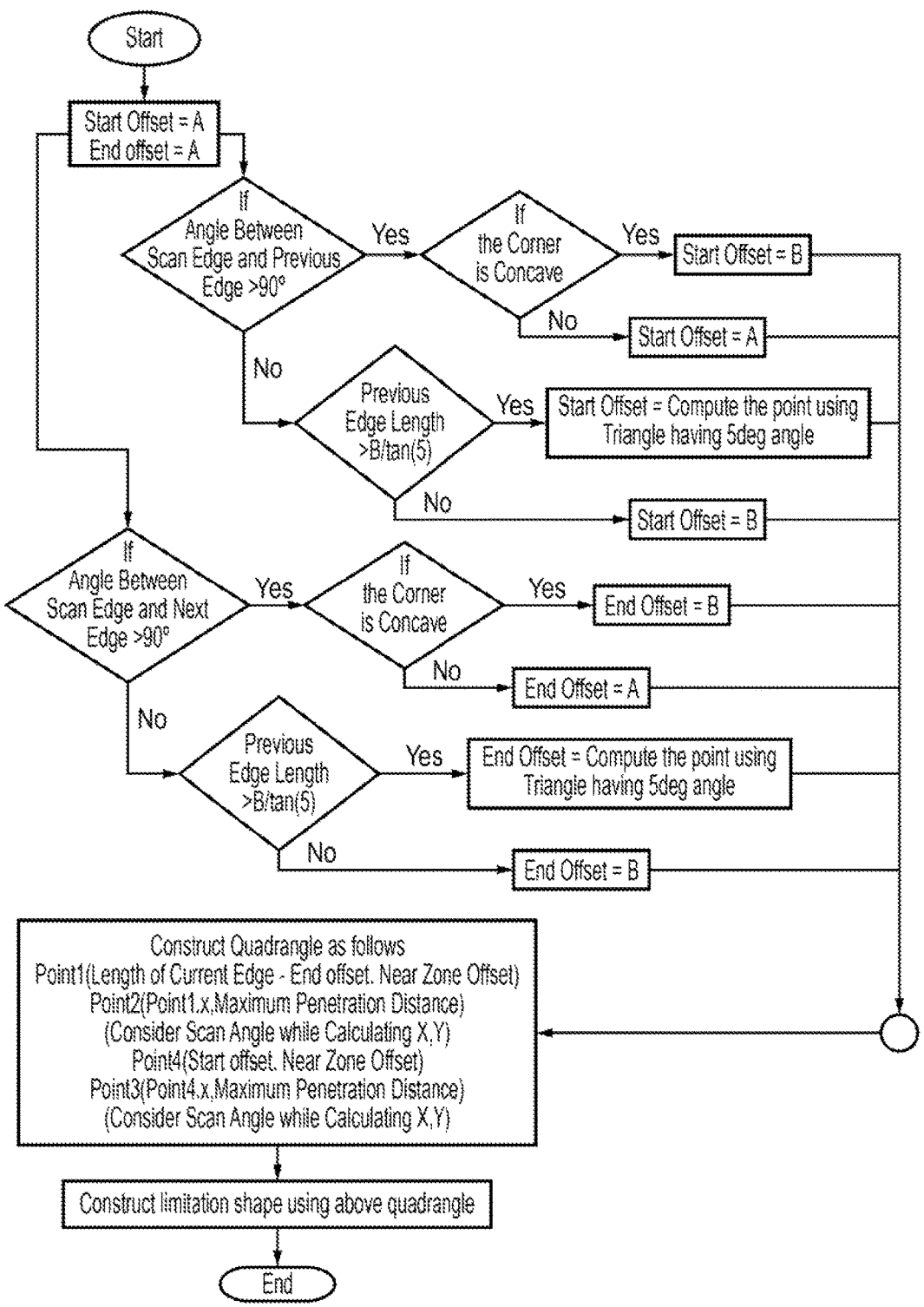
FIG. 5 is a flow chart describing a procedure for determining a quadrangular limitation shape for a given edge and a given beam angle.

FIG. 5 is a flow chart describing a procedure for determining a quadrangular limitation shape for a given edge (the "scan edge") and a given beam angle. The length of the limitation shape in the ultrasound beam direction is the maximum ultrasonic penetration depth. To construct the quadrangle, start and end scan points are calculated at the scan edge, the calculations being based on "external cliff" distances and concavity/convexity of the scan edge with neighbouring edges, and are to ensure appropriate standoffs to avoid interfering external geometries such as cliffs and corners.

The procedure is repeated SN times for an input geometry having N edges and S different beam angles per edge to produce SN limitation shapes.

Figure 6:
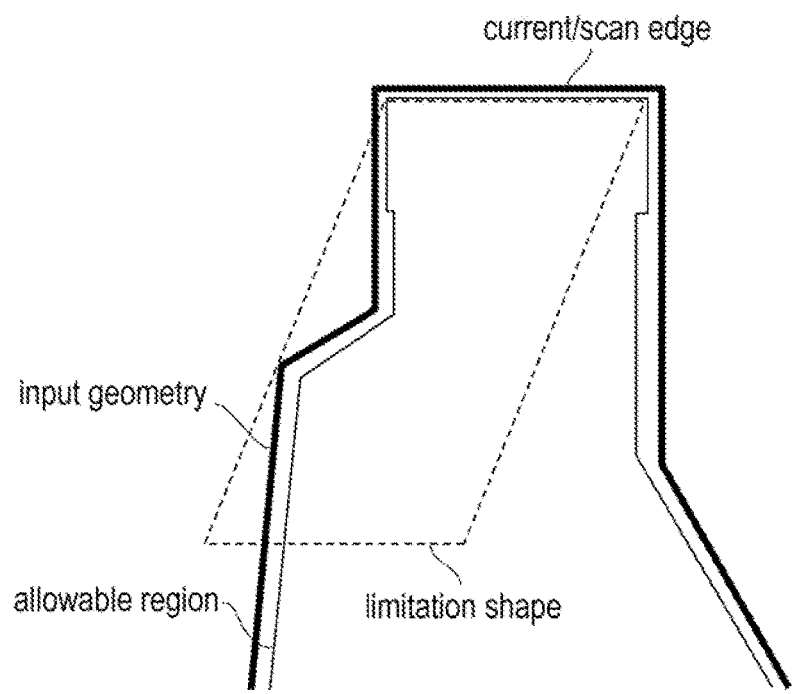
FIG. 6 shows schematically, for a given current/scan edge of an input geometry (thick line), the corresponding allowable region (thin line) and a corresponding limitation shape (dashed line) for an approximately 20° beam angle.

FIG. 6 shows schematically, for a given current/scan edge of an input geometry (thick line), the corresponding allowable region (thin line) and a corresponding limitation shape (dashed line) for an approximately 20° beam angle.

Combination of Allowable Regions with Limitation Shapes

The combination of the allowed regions with the limitation shapes is performed for each combination of the allowable region for a given edge and the limitation shapes for that edge. Thus for an input geometry having N edges and corresponding allowable regions, and having S limitation shapes per edge, the result is SN combinations.

Figure 7:
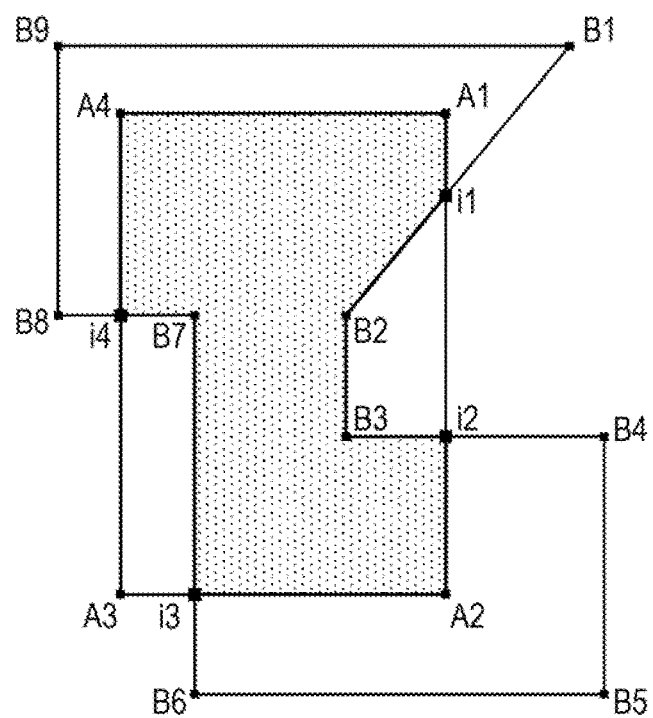
FIG. 7 shows two intersecting polygons and illustrates a procedure for computing their intersection polygon.

Each combination involves finding the intersection polygon of the respective limitation shape with the respective allowable region. The procedure for computing the intersection is illustrated in FIG. 7, and takes two polygons as its input, namely the limitation shape (bounded by A1, A2, A3, A4 in FIG. 7) and allowable region (bounded by B1, B2, B3, B4, B5, B6, B7, B8, B9 vertices in FIG. 7). The following steps are then performed:

Step 1: Select Edge 1 (A1-A2) of the limitation shape.

Step 2: Compute the number of intersections made by the selected edge with the allowable region (i1, i2).

Step 3: If the number of intersections is odd, then one of the vertices of the selected edge should be excluded. For example, Line A2-A3 has one Intersection (i3) hence A3 is the excluded vertex. Similarly, line A3-A4 also has one intersection (i4) hence A3 is the excluded vertex.

Step 4: Otherwise include the vertices of the allowable region between the odd intersection point and the next intersection point on the limitation shape. For example vertices B2 and B3 which are between intersection points i1 and i2.

Step 5: Select next edge (A2-A3) for intersection test and repeat all the steps from step 2.

Step 6: If all the edges of the limitation shape have been tested for intersection, form a new polygon with all the included vertices.

Figure 8:
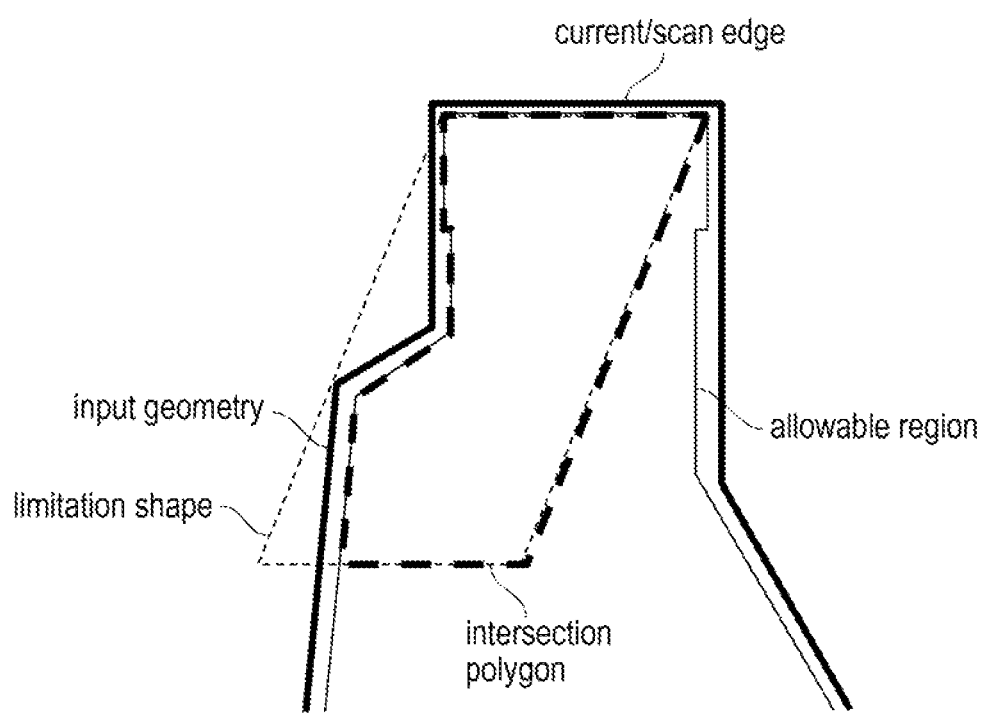
FIG. 8 shows with a thick dashed line the intersection polygon of the allowable region and the limitation shape of FIG. 6.
Figure 9:
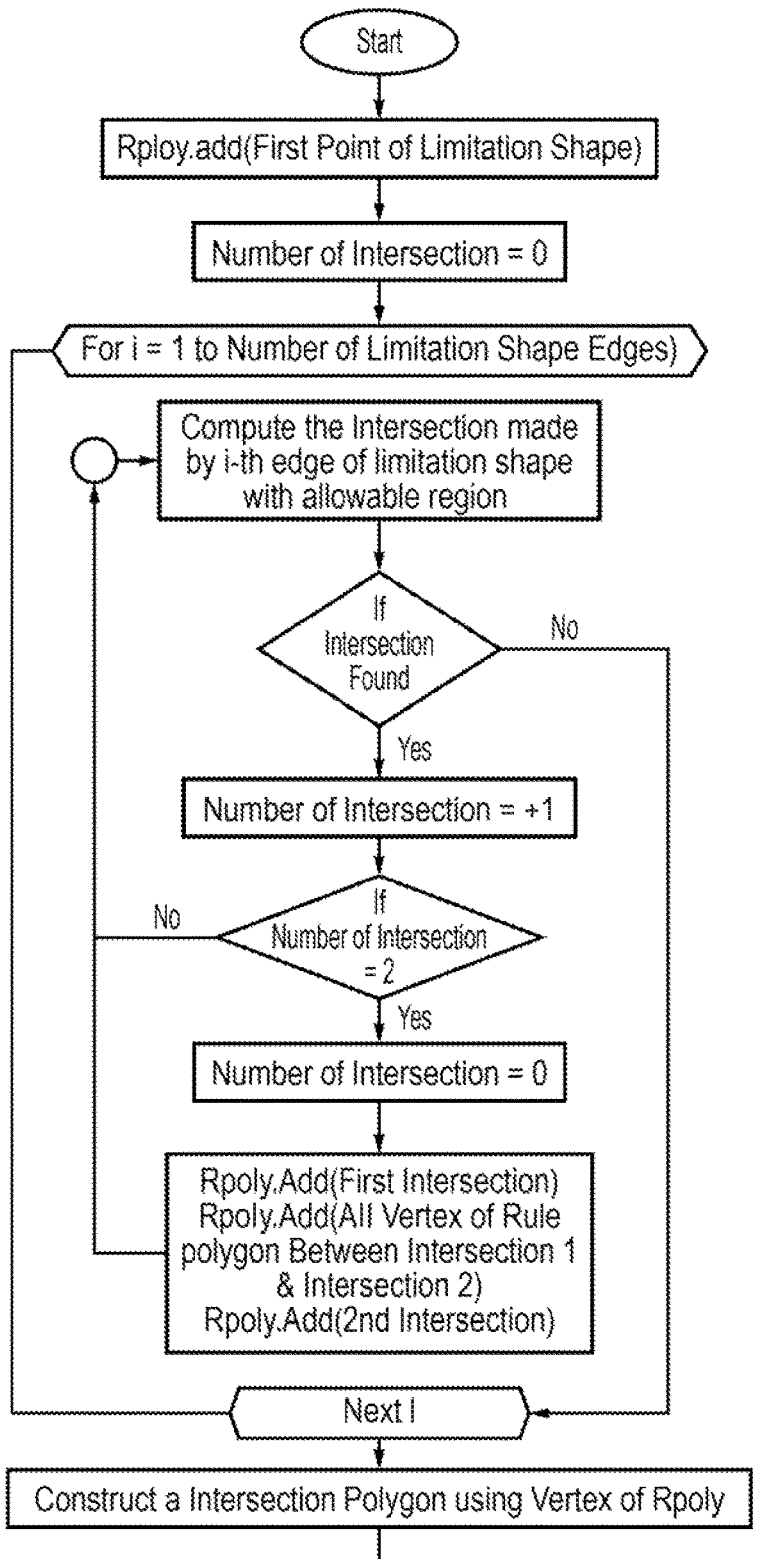
FIG. 9 is a flow chart describing the procedure for computing the intersection polygon.

Following these steps in the example of FIG. 7 results in an intersection polygon which is the shaded polygon with vertices A1, i1, B2, B3, i2, A2, i3, B7, i4, A4, A1. As another example, FIG. 8 shows with a thick dashed line the intersection polygon of the allowable region and the limitation shape of FIG. 6. FIG. 9 is a flow chart describing the procedure for computing the intersection polygon.

Ray Crop Filter

Figure 10:
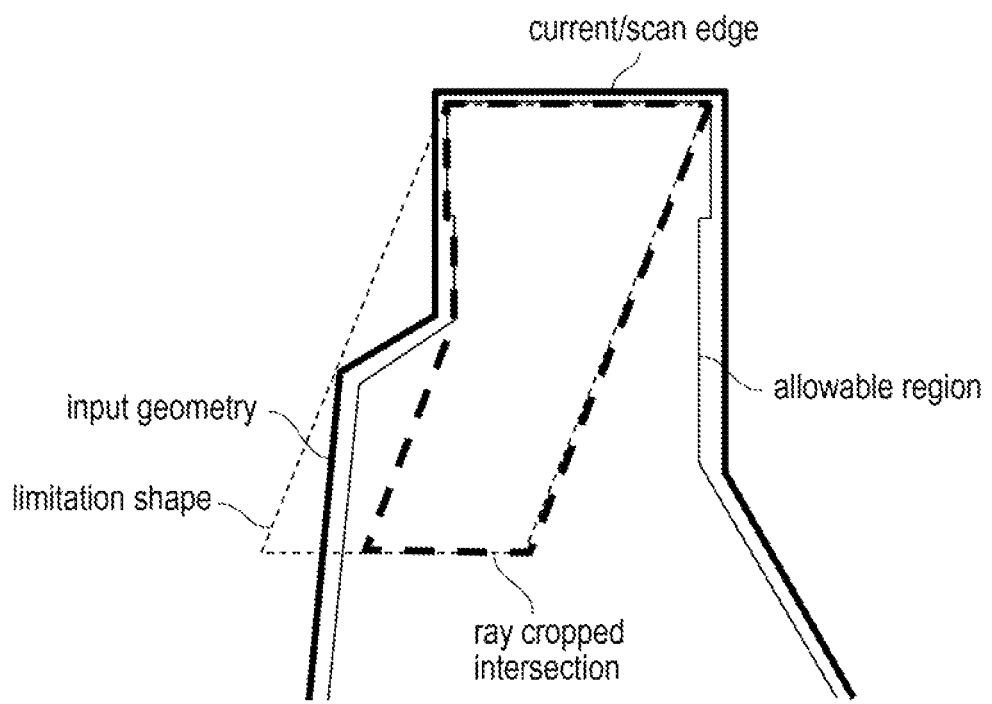
FIG. 10 shows the result of applying a ray crop filter to the intersection polygon of FIG. 8.

The resultant intersection polygons may not be fully inspectable regions because the ultrasonic beam cannot penetrate areas behind obstructing edges. Accordingly a ray crop filter can be applied to the intersections. FIG. 10 shows the result of applying such a filter to the intersection polygon of FIG. 8. The cropped intersection is again illustrated with a thick dashed line and can be compared with the original intersection polygon of FIG. 8.

The procedure for applying the ray crop filter has the following steps:

Step 1: Project each vertex of the intersection polygon onto the scan edge parallel to the beam direction.

Step 2: Compute the intersection of each projection line with the intersection polygon.

Figure 11:
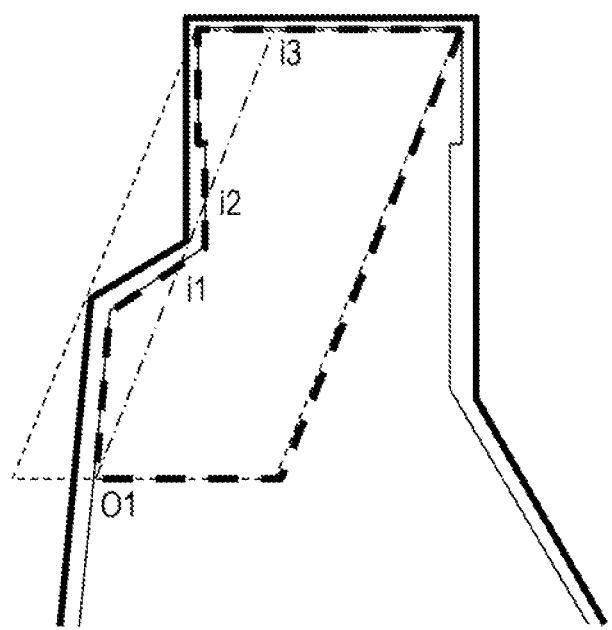
FIG. 11 shows multiple intersections i1, i2, i3 between a projected line (dot-dashed) from a vertex O1 and the intersection polygon, the construction being used in the ray crop filter to determine if the vertex is in an excluded list.
Figure 12:
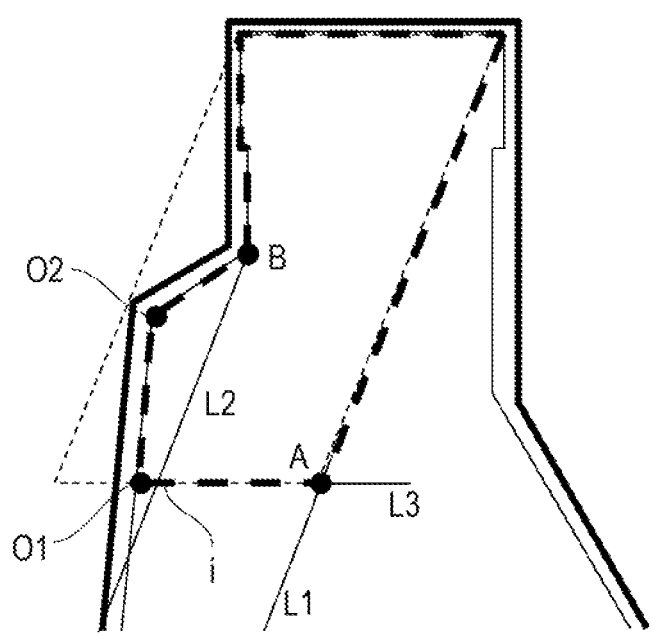
FIG. 12 shows excluded vertices O1, O2, a vertex A before the excluded list, a vertex B after the excluded list, and various line constructions used in the ray crop filter.

Step 3: If multiple intersections are found (meaning the projection line is passing through the outside of the intersection polygon), add that vertex of the intersection polygon into an excluded vertex list. FIG. 11 shows the multiple intersections i1, i2, i3 between the projected line (dot-dashed) from O1 and the intersection polygon. So, in this case O1 is added to the excluded list. FIG. 12 shows the excluded vertices O1, O2, the vertex A before the excluded list, and the vertex B after the excluded list.

Step 4: Following the computation of Steps 2 & 3, for each excluded list set the subroutine containing the following steps (4A-4E) is applied:

Step 4A: Draw a Beam Line L1 (as shown in FIG. 12) from the vertex before (A in FIG. 12). A "Beam Line" is defined as a line having the slope of the beam direction and the length of maximum penetration distance.

Step 4B: Check for an intersection between the Beam Line L1 and the polygon formed by the excluded list and the vertices before and after the excluded list (i.e. polygon A-O1-O2-B in FIG. 12). This polygon is known as the Test Range polygon. If an intersection found, term the Beam Line L1 as the "A-Line" or else draw an Edge Line from the vertex A (line L3 in FIG. 12) and term it as the "A-line". An "Edge Line" is defined as a line having the slope of the given scan edge and unit length.

Step 4C: Draw another Beam Line L2 (as shown in FIG. 12) from the vertex after (B in FIG. 12).

Step 4D: Check for an intersection between the Beam Line L2 and the Test Range polygon (A-O1-O2-B). If an intersection found, term the Beam Line L2 as the "B-Line" or else draw an Edge Line from the vertex B and term it as the "B-Line".

Step 4E: Calculate the intersection point (i in FIG. 12) between the A-Line and the B-Line. Replace the excluded list vertices (O1, O2 in FIG. 12) with the calculated intersection point in the intersection polygon.

Figure 13:
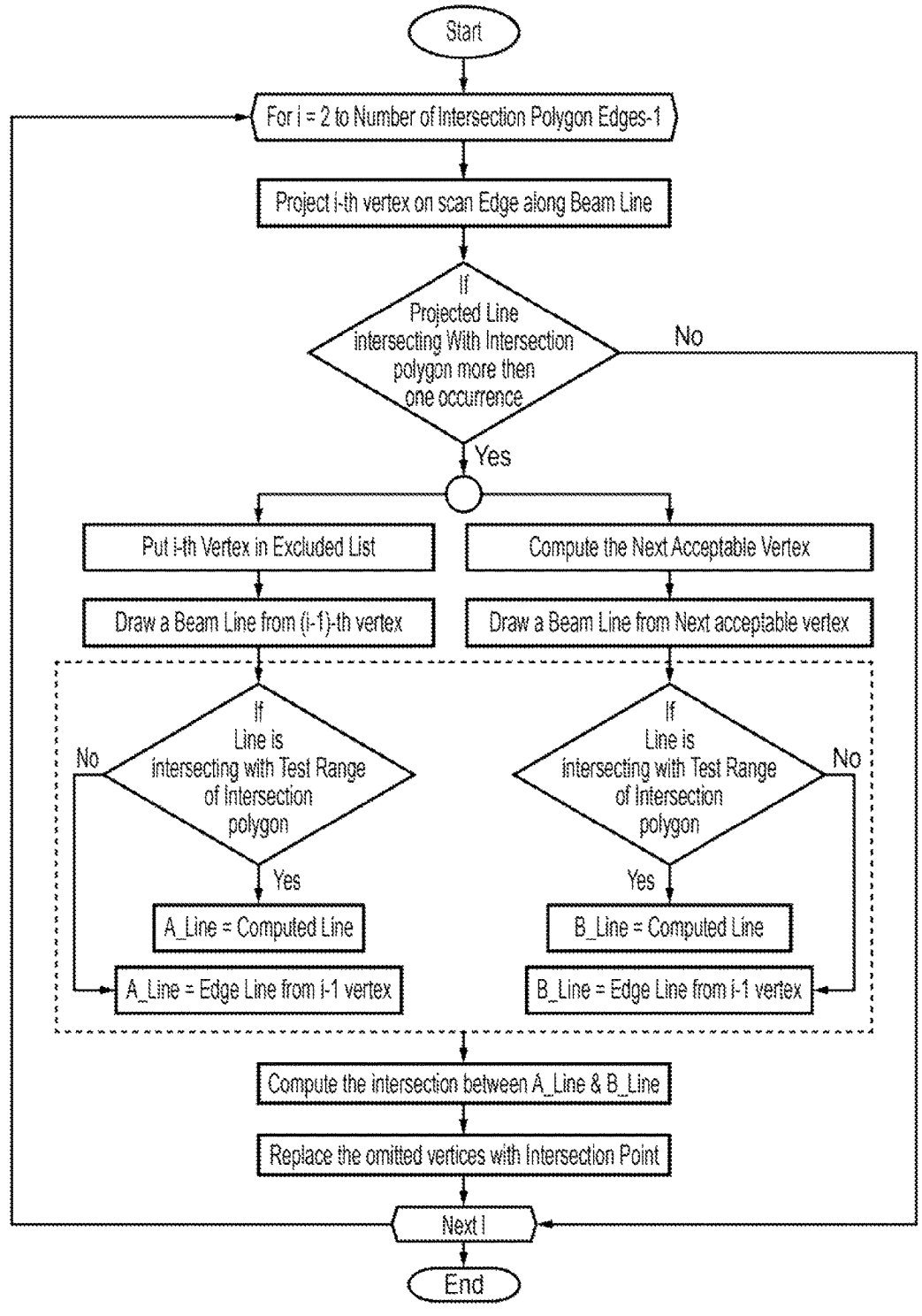
FIG. 13 is a flow chart describing the procedure for applying the ray crop filter.

FIG. 13 is a flow chart describing the procedure for applying the ray crop filter.

Trim for Minimum Beam Width

Figure 14:
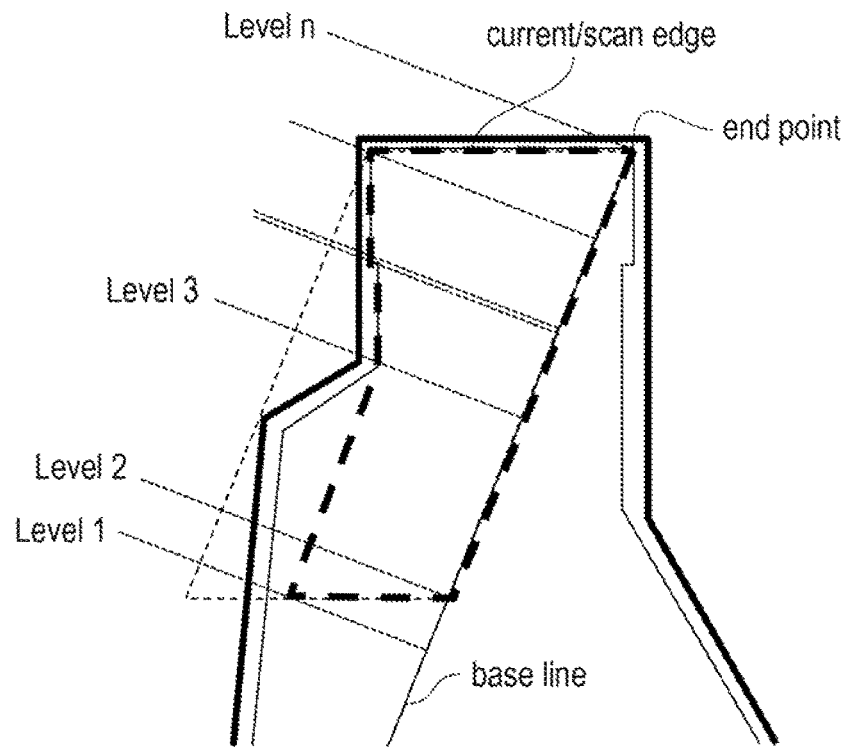
FIG. 14 shows constructions used in a procedure for applying a trim for minimum beam width.

Even after applying the ray crop filter, the intersection polygons may not be fully inspectable regions because the ultrasonic beam cannot penetrate beyond a specific converging beam width. Hence the polygon obtained after the ray crop filter may be further refined to incorporate this constraint. The default value for the minimum converging beam width can be specified at 10 mm. The procedure for the trim for minimum beam width has the following steps:

Step 1: Draw a base line of infinite length (shown in FIG. 14) from the end point of the given scan edge in the direction of the beam.

Step 2: Draw perpendicular cross lines (shown as dotted lines in FIG. 14) from each vertex of the intersection polygon onto the base line. Extend the lengths of the cross lines by a pre-defined value (more than width of the intersection polygon) away from the base line.

Step 3: Select the farthest cross line from the end point of the given scan edge and perform an intersection test between the selected cross line and the intersection polygon. The intersection test determines the number of times the cross line intersects the edges of the polygon.

Step 4: The number of intersection points are always even when a straight line passes through a closed polygon. Hence, the length of the enclosed intersection segment can be calculated using these intersection points.

Step 5: If length of the intersection segment is less than the minimum beam width (e.g. 10 mm) exclude the vertex or vertices available on the same level of cross line.

Step 6: Identify the next cross line level moving towards the scan edge and recalculate the intersection segment of the given cross line. If the length of the segment is less than the minimum beam width, exclude the vertices available in the selected cross line level. Repeat this step until the length of the computed intersection segment is greater than the minimum beam width.

Step 7: Using the method of similar triangles calculate a new cross line and make it a new edge of the intersection polygon.

Step 8: Repeat steps 1 to 7 until no further trimming.

Figure 15:
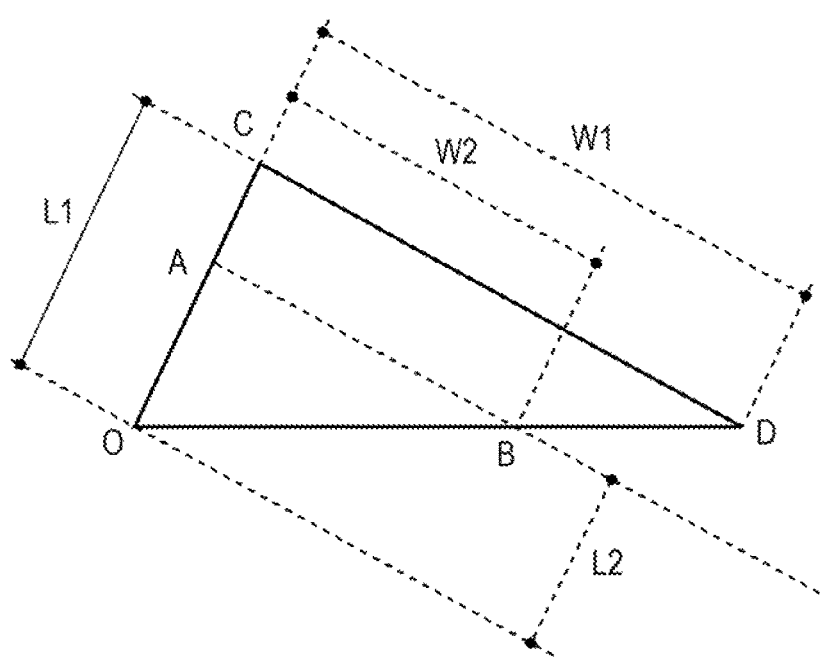
FIG. 15 illustrates a method of similar triangles used in the trimming procedure.

FIG. 15 illustrates the method of similar triangles from Step 7. The distance L1 is the distance between Level 1 and Level 2, W1 is the length of cross line segment at Level 2, and W2 is the minimum beam width. The unknown value L2 can be computed using the relationship W1/L1=W2/L2 due to the similarity of triangle AOB and triangle COD. Once L2 is calculated, the equation of line AB is determined by translating the line CD by a distance of (L1-L2) in a direction parallel to the base line.

Figure 16:
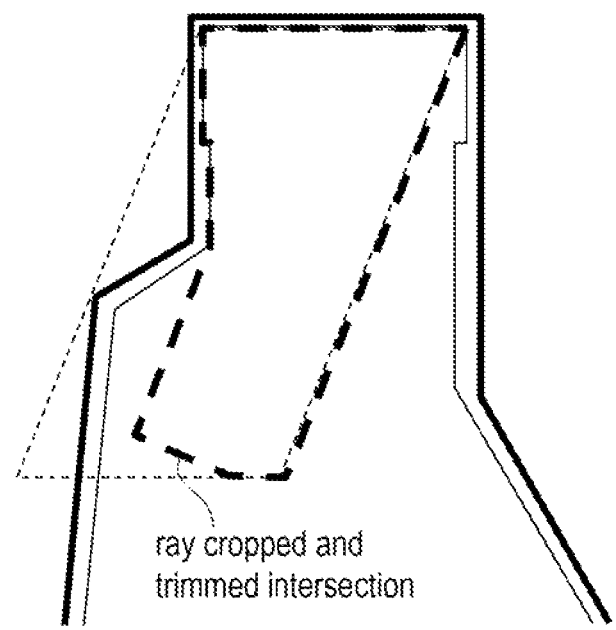
FIG. 16 shows the result of applying the ray crop filter and the trim for minimum beam width to the intersection polygon of FIG. 8.
Figure 17:
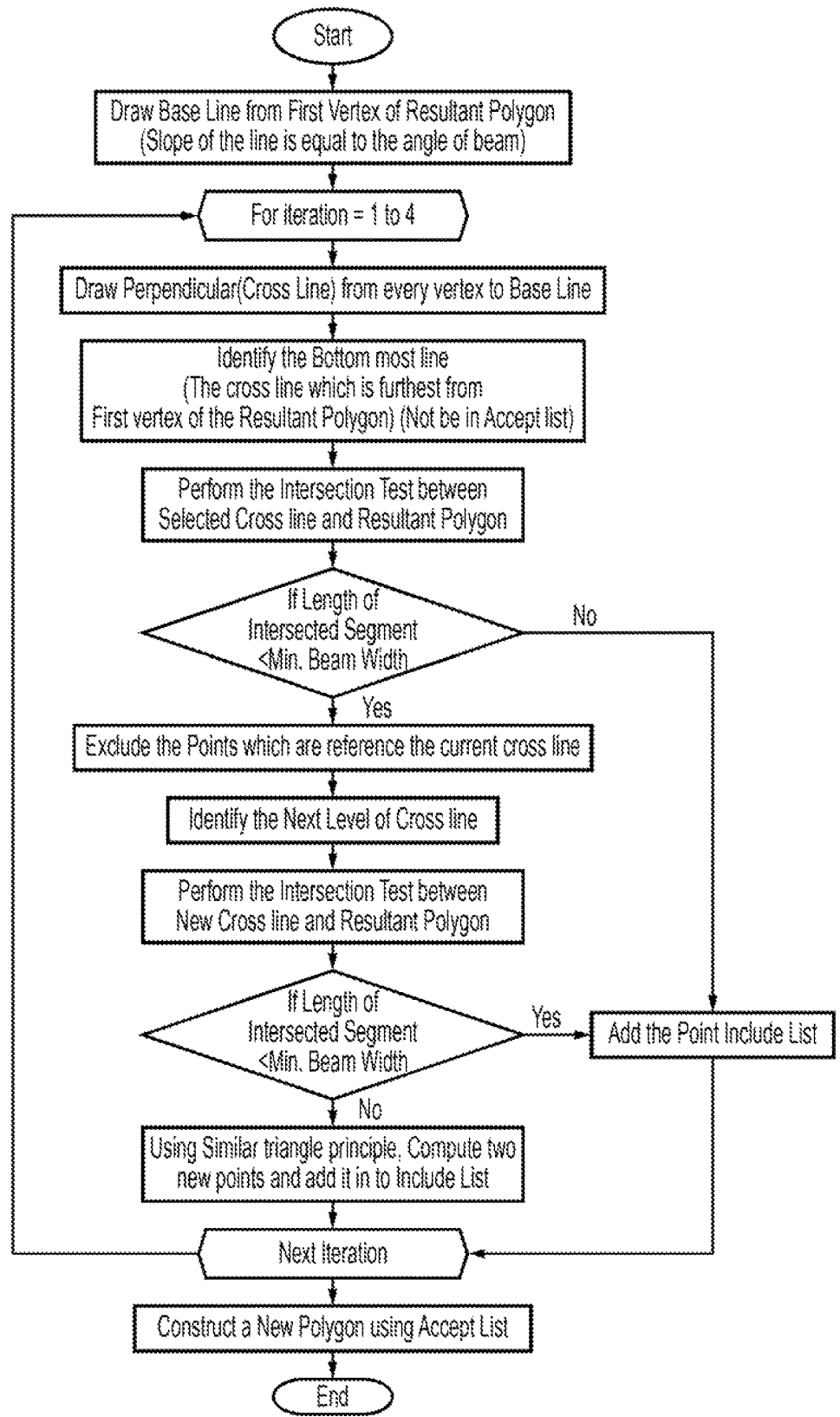
FIG. 17 is a flow chart describing the procedure for applying the trim for minimum beam width.

FIG. 16 shows the intersection polygon of FIG. 8 after ray crop filtering and trimming for minimum beam width. FIG. 17 is a flow chart describing the procedure for applying the trim for minimum beam width.

Determination of Ultrasonic Inspectability

The cropped and trimmed intersection polygons are classified as inspectable regions, and are then used to determine the overall ultrasonic inspectability of the target geometry.

More particularly, the inspection rules specify that the target geometry is ultrasonic inspectability when all parts of the geometry are covered by at least a predetermined minimum number of inspectable regions. Typically three is the minimum number to ensure with a high degree of probability that an anomaly at a given point will be detected by ultrasonic inspection.

Figure 18:
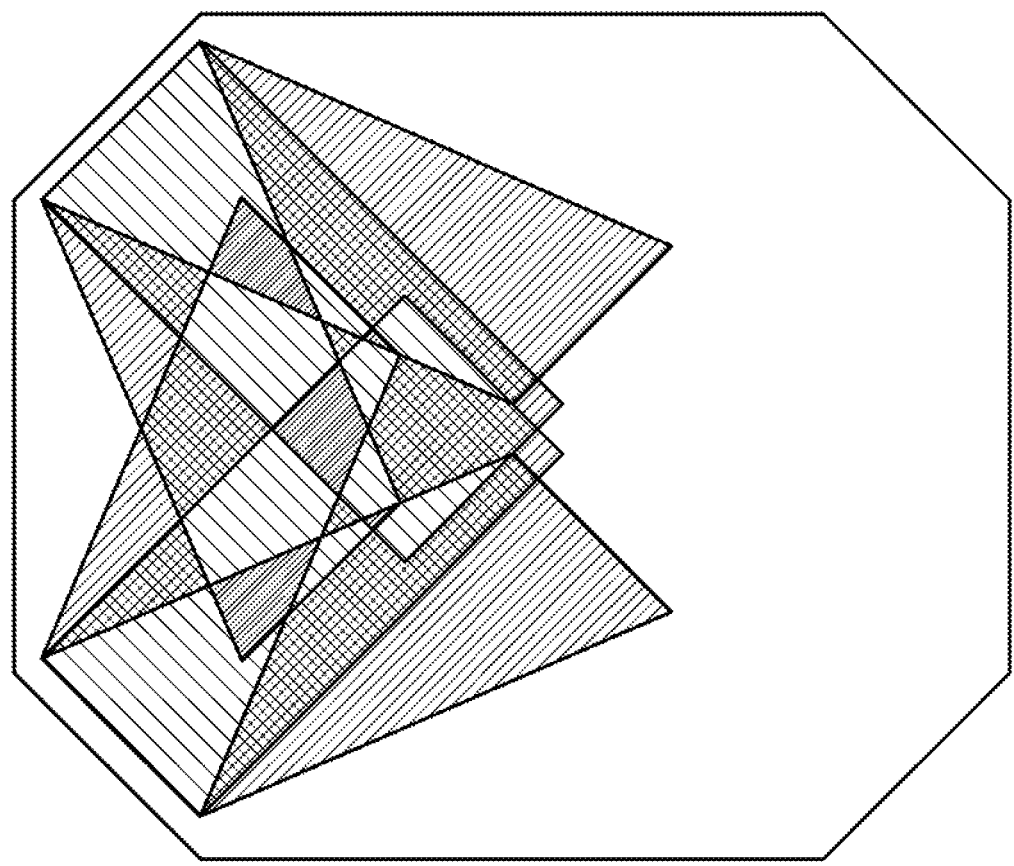
FIG. 18 shows schematically overlayed inspectable regions of two edges of an eight-sided input geometry.

Accordingly, the inspectable regions are overlayed on each other and the target geometry in their relative positions. FIG. 18 shows schematically the overlayed inspectable regions of two edges of an eight-sided input geometry. There are three inspectable regions per edge. The darker the shading at a given position, the more inspectable regions overlap at that position. In this way it is straightforward to determine if all parts of a target geometry have sufficient coverage.

General Comments

The above description provides preferred exemplary embodiment(s) only, and is not intended to limit the scope, applicability or configuration of the invention. Rather, the above description of the preferred exemplary embodiment(s) provides those skilled in the art with an enabling description for implementing a preferred exemplary embodiment of the invention, it being understood that various changes may be made in the function and arrangement of elements without departing from the scope of the invention.

Thus, for example, instead of an axisymmetric disc, the supplied part and/or the final component may be non-axisymmetric. In this case, the input geometry can comprise multiple different 2D polygons, and the target geometry can likewise comprise multiple different 2D forms. The above procedure can, however, simply be repeated for each combination of an input geometry 2D polygon and a target geometry 2D form.

Specific details are given in the above description to provide an understanding of the embodiments. However, it will be understood by one of ordinary skill in the art that embodiments maybe practiced without these specific details. For example, well-known circuits, processes, algorithms, structures, and techniques may be shown without unnecessary detail in order to avoid obscuring the embodiments.

Embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

As disclosed herein, the term "computer readable medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The invention claimed is:

1. A method of determining the ultrasonic inspectability of a supplied part out of which a final component is to be machined, the method including the steps of:
   providing a set of inspection rules for ultrasonic inspection of the supplied part;
   providing an input geometry for the supplied part in the form of at least one 2D polygon, the supplied part being ultrasonically inspectable by scanning an ultrasonic probe at one or more different ultrasound beam angles along faces of the supplied part corresponding to polygon edges of the input geometry, whereby a complete ultrasonic inspection of the supplied part comprises a number of scans equal to the sum, over all the edges, of all the beam angles used for a given edge;
   providing a target geometry which is at least one further 2D form defining the shape and position of the machined final component within the input geometry;
   for each edge of the input geometry, determining a respective allowable region of the input geometry that defines those parts of the input geometry which can be ultrasonically inspected from that edge without infringing the inspection rules;
   for each combination of a given ultrasound beam angle and a given edge of the input geometry, determining a respective limitation shape which is bounded at one side by the given edge and extends from that edge in the direction of the beam to a boundary at a penetration depth of the ultrasound in the input geometry;

for each edge of the input geometry, combining the one or more limitation shapes for that edge with the allowable region for that edge to determine one or more inspectable regions of the input geometry associated with that edge, each inspectable region thereby corresponding to a respective one of the scans of the complete ultrasonic inspection; and overlaying the inspectable regions in their relative positions on the target geometry, whereby the supplied part is determined to be ultrasonically inspectable when all parts of the target geometry are overlayed by at least a predetermined minimum number of the inspectable regions.

2. The method according to claim 1, wherein the supplied part and the final component are axisymmetric, the input geometry being a longitudinal cross-section through the supplied part, and the target geometry being a longitudinal cross-section through the final component.

3. The method according to claim 1, wherein the supplied part and/or the final component are non-axisymmetric, the input geometry being plural longitudinal cross-sections through the supplied part, and the target geometry being plural longitudinal cross-sections through the final component.

4. The method according to claim 1, wherein the combining step includes the sub-step of calculating, for each combination of a limitation shape and the allowable region, the intersection polygon of that limitation shape with the allowable region.

5. The method according to claim 4, wherein the combining step further includes the sub-step of cropping the intersection polygon to remove parts thereof which cannot be penetrated by the ultrasound beam due to obstructions.

6. The method according to claim 4, wherein the combining step further includes the sub-step of trimming the intersection polygon to remove parts thereof which cannot be penetrated by the ultrasound beam due to the finite beam width.

7. A manufacturing process including the steps of:
designing a supplied part;
performing the method of claim 1 to determine that the supplied part is ultrasonically inspectable;
producing the supplied part; and
ultrasonically inspecting the supplied part.

8. The manufacturing process according to claim 7, further including the step of machining the inspected supplied part to produce the final component therefrom.

9. A computer program comprising code which, when run on a computer, causes the computer to perform the method of claim 1.

10. A computer readable medium storing a computer program comprising code which, when run on a computer, causes the computer to perform the method of claim 1.

11. A computer system programmed to perform the method of claim 1.

12. A manufacturing process including the steps of:
designing a supplied part;
performing a method to determine that the supplied part is ultrasonically inspectable, the method including the steps of:
    providing a set of inspection rules for ultrasonic inspection of the supplied part;
    providing an input geometry for the supplied part in the form of at least one 2D polygon, the supplied part being ultrasonically inspectable by scanning an ultrasonic probe at one or more different ultrasound beam angles along faces of the supplied part corresponding to polygon edges of the input geometry, whereby a complete ultrasonic inspection of the supplied part comprises a number of scans equal to the sum, over all the edges, of all the beam angles used for a given edge;
    providing a target geometry which is at least one further 2D form defining the shape and position of the machined final component within the input geometry;
    for each edge of the input geometry, determining a respective allowable region of the input geometry that defines those parts of the input geometry which can be ultrasonically inspected from that edge without infringing the inspection rules;
    for each combination of a given ultrasound beam angle and a given edge of the input geometry, determining a respective limitation shape which is bounded at one side by the given edge and extends from that edge in the direction of the beam to a boundary at a penetration depth of the ultrasound in the input geometry;
    for each edge of the input geometry, combining the one or more limitation shapes for that edge with the allowable region for that edge to determine one or more inspectable regions of the input geometry associated with that edge, each inspectable region thereby corresponding to a respective one of the scans of the complete ultrasonic inspection; and
    overlaying the inspectable regions in their relative positions on the target geometry, whereby the supplied part is determined to be ultrasonically inspectable when all parts of the target geometry are overlayed by at least a predetermined minimum number of the inspectable regions to determine that the supplied part is ultrasonically inspectable;
the manufacturing process further comprising:
    producing the supplied part; and
    ultrasonically inspecting the supplied part.

13. The manufacturing process according to claim 12, further including the step of machining the inspected supplied part to produce the final component therefrom.

* * * * *